United States Patent
Ungs

(10) Patent No.: US 6,569,185 B2
(45) Date of Patent: May 27, 2003

(54) CONTINUOUS INFUSION TECHNIQUE FOR ARTERIAL SEALING

(76) Inventor: Mark T. Ungs, 4671Woodridge Rd., Minnetonka, MN (US) 55345

( * ) Notice: Subject to any disclaimer, the term of this patent is extended or adjusted under 35 U.S.C. 154(b) by 101 days.

(21) Appl. No.: 09/784,706

(22) Filed: Feb. 15, 2001

(65) Prior Publication Data

US 2002/0111651 A1 Aug. 15, 2002

(51) Int. Cl.[7] .............................................. A61B 17/58
(52) U.S. Cl. ..................................... 606/213; 606/214
(58) Field of Search ............................... 606/213, 214, 606/215, 216, 191; 604/4.01, 6.07, 6.16, 19, 21, 506–511, 522; 128/898

(56) References Cited

U.S. PATENT DOCUMENTS

| | | |
|---|---|---|
| 4,852,568 A | 8/1989 | Kensey |
| 5,292,332 A | 3/1994 | Lee |
| 5,626,601 A | 5/1997 | Gershony et al. |
| 5,653,730 A * | 8/1997 | Hammerslag ................ 606/214 |
| 5,676,689 A * | 10/1997 | Kensey et al. ............... 606/213 |
| 5,725,498 A * | 3/1998 | Janzen et al. ................ 606/213 |
| 5,741,223 A * | 4/1998 | Janzen et al. ................ 606/213 |
| 5,814,066 A | 9/1998 | Spotnitz |
| 5,830,130 A * | 11/1998 | Janzen et al. ................ 606/213 |
| 6,045,570 A | 4/2000 | Epstein et al. |
| 6,090,130 A | 7/2000 | Nash et al. |
| 6,159,232 A | 12/2000 | Nowakowski |
| 6,287,323 B1 * | 9/2001 | Hammerslag ................ 606/214 |
| 6,296,658 B1 * | 10/2001 | Gershony et al. ........... 606/213 |
| 6,325,789 B1 * | 12/2001 | Janzen et al. ................ 606/215 |

FOREIGN PATENT DOCUMENTS

WO     WO 98/17179     4/1998

* cited by examiner

Primary Examiner—Gloria M. Hale
(74) Attorney, Agent, or Firm—Todd P. Messal

(57) ABSTRACT

A method of performing a vascular closure whereby closure material is safely injected into the blood vessel and into the vascular opening.

22 Claims, 2 Drawing Sheets

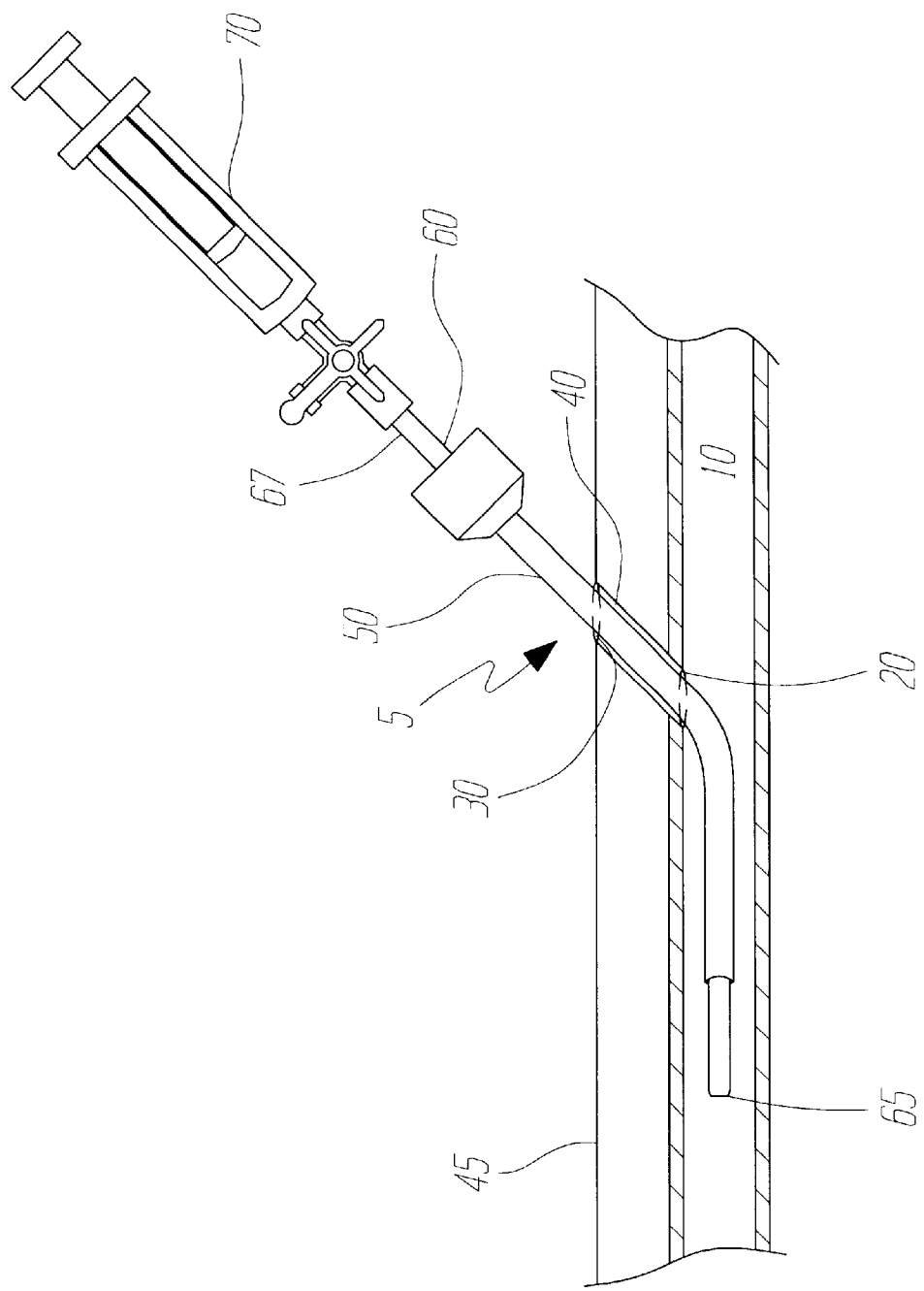

CONTINUOUS INFUSION TECHNIQUE FOR ARTERIAL SEALING

FIELD OF THE INVENTION

The present invention generally relates to the field of vascular closure devices. More specifically, this invention may be used to close openings in the vasculature created to perform intravascular procedures. Those skilled in the art will recognize the benefits of applying the present invention to similar fields not discussed herein.

BACKGROUND OF THE INVENTION

A variety of procedures are currently performed which access various portions of the human body through the vasculature. These procedures are begun by puncturing the skin and providing access into an artery or vein. Access to the artery may be provided by cutting open a portion of the body and exposing the artery. That artery may then be accessed by puncturing the artery. Alternatively, access to the artery may be gained by a technique commonly known as the Seldinger technique. Seldinger invented a system which includes a needle, sheath and dilator to provide a resealable access point into the vasculature. Common points of vascular access include the brachial artery accessed just above the elbow, the radial artery approach accessed just above the wrist, or the femoral artery approach accessed just below the groin.

One of the most common procedures is balloon angioplasty. Balloon angioplasty is typically performed through a sheath placed in a vascular access point. After a sheath is firmly located in the vascular access point, a guide catheter is inserted through the sheath and into the vascular system. The guide catheter is then typically advanced under fluoroscopy to the ostium of the left or right coronary artery.

After the distal end of the guide catheter is satisfactorily located in the ostium of a coronary artery, a guide wire is inserted through the sheath, inside the guide catheter and advanced through the guide catheter until the distal end of the guide wire emerges from the distal end of the guide catheter. The guide wire is further advanced through the coronary vasculature until it reaches a portion of vasculature which is in need of treatment. Commonly, the vasculature will be partially or completely obstructed by stenotic material which may be comprised of plaque or other material. Typically the distal end of the guide wire is advanced beyond the area of treatment.

After the guide wire is located in a desired position, a balloon catheter is inserted into the sheath. The balloon catheter is threaded over the guide wire and inside the guide catheter. The distal end of the balloon catheter is advanced to the treatment site and located such that the balloon is positioned within the stenosis. Once the balloon is in position it is inflated with fluid and thereby expanded. Expansion of the balloon forces any stenotic material away from the center of the blood vessel and thereby improves the patency of the artery which is being treated. Once dilatation is complete, the balloon catheter is removed.

This procedure may be repeated with different size balloons or in multiple sits within the vasculature depending upon patient need. However, once the procedure is complete, the physician will remove the balloon catheter, guide wire, guide catheter and ultimately the sheath itself. Sheaths may range in size from 4–9 French. Depending upon the size of the sheath, a relatively large hole has been made in the artery at the vascular access site. Without further treatment, the patient would likely bleed to death through the hole made when the sheath is removed.

There are several methods of treating the vascular wound once the sheath has been removed. The most common method of treatment is simple pressure. This method may include a pressure dressing, physical pressure applied by an attendant, or pressure applied by some sort of apparatus. While this method is ultimately effective, it may take several hours to safely close the vascular access site such that the patient is able to move about.

Alternative systems to pressure have also been developed. These systems commonly known include heat sealing, lasers, suture based systems, or various types of plugs or glues. Plugs may be made in many different shapes and may be created from a variety of materials. No matter what the material or the shape of the plug, accurate placement of the plug is desirable. Placement is particularly import with prior art plug systems which use some portion of the patient's blood to form a clot or other obstructions. Prior art closure systems such as U.S. Pat. No. 5,626,601 to Gershoney. This particular system uses a balloon which can be inflated to prevent the closure material from entering the vessel. Once the plug material has been injected into the vascular access site and partially solidifies, the balloon is deflated and pulled through the plug material. Another prior art closure invented by Kensey and described in U.S. Pat. No. 5,676,689, uses a biodegradable backstop to prevent a plug from entering the vessel. This backstop is left in the vessel until it eventually degrades. While many systems exist, a system which provides better placement of the plug material may be desirable.

While one particular vascular procedure has been described as background, one skilled in the art will appreciate that the inventive technique may be used for any variety of intravascular or other intra-body access procedures known in the art.

SUMMARY OF THE INVENTION

The present invention overcomes the deficiencies of the prior art by providing a method to safely deliver a closure system without the use of prior art protection devices the patient.

BRIEF DESCRIPTION OF THE DRAWINGS

FIG. 1 depicts a cross-section of an embodiment of a closure device inserted into a vascular opening.

DETAILED DESCRIPTION OF THE INVENTION

Figure 3:
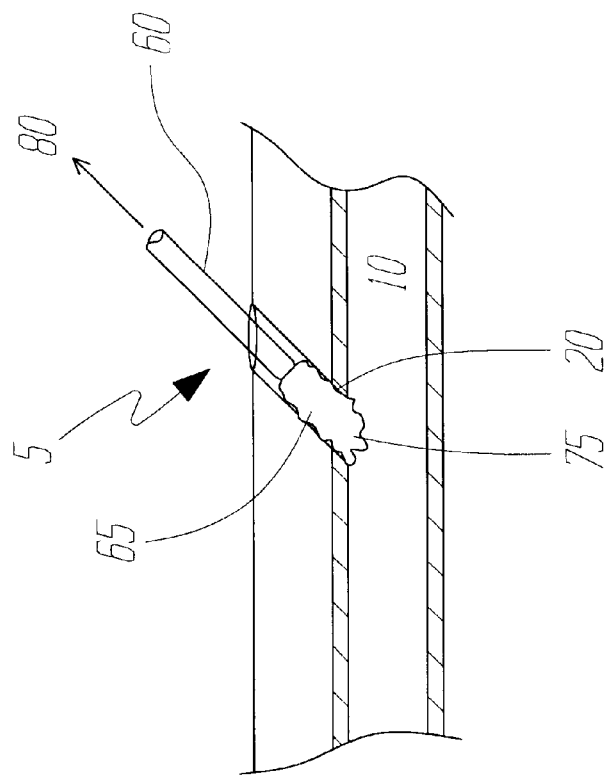
FIG. 3 depicts the closure method of FIG. 2 wherein the closure device has been further removed from the vascular opening.

The following detailed description should be read with reference to the drawings in which like elements in different drawing are numbered identically. The drawings, which are not necessarily to scale, depict selected embodiments and are not intended to limit the scope of the invention.

Examples of constructions, materials, dimensions, and manufacturing processes are provided for selected elements. All other elements employ that which is known to those skilled in the field of the invention. Those skilled in the art will recognize that many of the examples provided have suitable alternatives that may also be used.

An embodiment of the inventive method, may be used with a vascular closure device as described in U.S. Pat. No. 6,159,232 which is herein incorporated by reference.

Referring now to FIG. 1, a vascular opening 5 is depicted in a human body. Blood vessel 10 may have a vessel opening 20 which may be aligned with a skin opening 30 in the skin 45 of a patient. Skin opening 30 may be in any portion of the body which corresponds to a desired intravascular procedure. Vascular opening 5 may include but is not limited to an opening in the femoral artery located near the groin, an opening in the brachial artery located near the elbow, an opening in the radial artery located near the wrist, or an opening in the jugular artery located near the neck.

Located between the skin opening 30 and the vessel opening 20 is a tissue tract 40. Tissue tract 40 may vary in length depending upon the particular point of the vasculature which is being accessed and the relative distance between the skin 45 and the vessel 10. The diameter of tissue tract 40 may roughly correspond to the diameters of vessel opening 20 and skin opening 30. The diameter of vessel opening 20 and skin opening 30 may vary depending upon the particular intravascular procedure which may be performed and the vascular access point. Typical vessel opening 20 may be 4–9 French.

Most intravascular procedures may include a sheath 50 which may be inserted into blood vessel 10 via tissue tract 40. Sheaths are well known in the art and are commercially available in a variety of sizes and lengths. An example of a sheath is the Pinacle® sold by Boston Scientific Corporation.

Following the intravascular procedure, a closure device 60 may be inserted through sheath 50 until distal end 65 is positioned within blood vessel 10. A syringe 70 may be connected to a proximal end 67 of closure device 60. Alternatively, any system commonly known in the art may be used to remove blood from the blood vessel 10. Blood which is removed from the blood vessel 10 may be treated to create a closure material. Closure material may be formed by the invention disclosed in U.S. Pat. No. 6,159,232 or other procedures known in the art.

Figure 2:
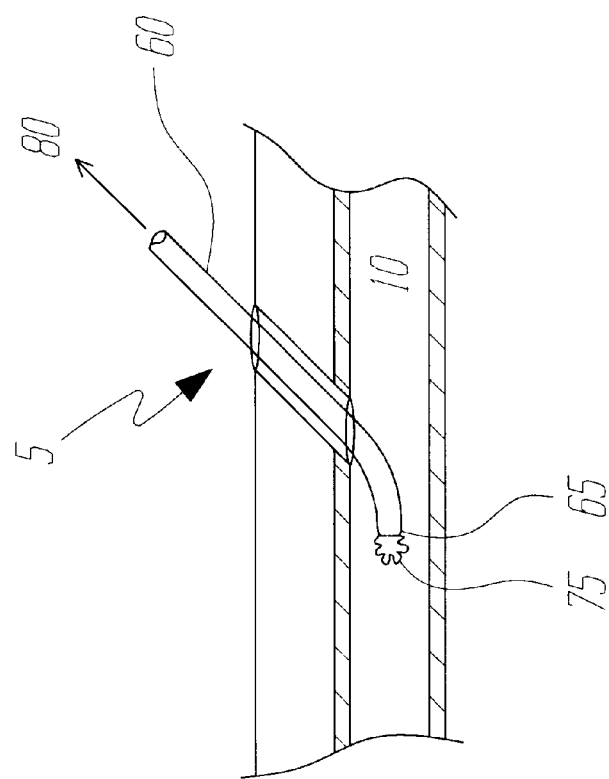
FIG. 2 depicts a cross-section of a vascular opening where a closure material is injected into the vascular opening using the closure device of FIG. 1.

While FIG. 1 is depicted with sheath 50, the inventive method may also be performed without sheath 50 or after sheath 50 has been removed. FIG. 2 depicts closure device 60 in vessel 10 without sheath 50 present. Closure material 75 may then be injected as closure device 60 is removed from vascular opening 5. Closure material 75 may be injected continuously while closure device 60 is removed from vascular opening 5. Sheath 50 may generally be removed along a path depicted by arrow 80.

Alternatively, a bolus of closure material 75 may be injected prior to closure device 60 moving. Once injection of closure material 75 has been stopped, closure device 60 may be retracted proximally, but not withdrawn from the vascular opening 5, and another bolus of closure material 75 may be injected. This process may be repeated in a step-wise fashion as desired by the user.

FIG. 3 shows closure device 60 further removed from vascular opening 5 in the general direction indicated by arrow 80. Distal end 65 has been withdrawn from vessel 10 along tissue tract 40. While distal end 65 is moving, closure material 75 may be injected. Closure material 75 may thereby be partially injected into vessel 10 and also into tissue tract 40. By injecting closure material 75 while closure device 60 is removed, the user of the inventive method may insure that closure material 75 is injected just outside of vessel opening 20. Further injection of closure material 75 may occur as device 60 is completely removed or may only occur near vessel opening 20. Following the completion of injecting of closure material 75, pressure or a bandage may be applied to vascular opening 5 depending upon the effectiveness of closure material 75.

While the specification describes the preferred designs, materials, methods of manufacture and methods of use, those skilled in the art will appreciate the scope and spirit of the invention with reference to the appended claims.

I claim:

1. A method for sealing a vascular access comprising:
   providing a closure device, the closure device having a distal end and a proximal end;
   withdrawing the closure device from the vascular access; and
   activating a closure material while the distal end of the closure device is located within a blood vessel.

2. The method of claim 1 wherein the closure device further comprises a tubular body having a lumen therethrough.

3. The method of claim 1 wherein the closure device further comprises a closure material.

4. The method of claim 3 wherein the closure material comprises human blood components.

5. The method of claim 3 wherein the closure material consists of human blood components.

6. The method of claim 3 further comprising injecting a closure material into the blood vessel.

7. The method of claim 6 further comprising injecting a closure material into a body channel located outside of the blood vessel.

8. The method of claim 7 further comprising:
   withdrawing human blood from the blood vessel;
   treating the human blood; and
   injecting human blood components made from the treated human blood in the vascular access.

9. A method of closing a vascular access, wherein the vascular access comprises a blood vessel having a lumen therein and an opening, a tissue tract between the vessel opening and an incision in the skin, the method comprising:
   providing a vascular access sheath having a lumen therethrough;
   placing the sheath in the vascular access such that a distal portion of the sheath is inserted into the blood vessel;
   providing a closure device having an elongate tubular body sized to fit within the sheath, a lumen located within the closure device and in fluid communication between a distal end of the closure device and a proximal end of the closure device;
   inserting the closure device into the lumen of the sheath such that the distal end of the closure device emerges from the distal end of the sheath and into the blood vessel; and
   actuating the closure device while the distal end of the closure device and the sheath are located within the blood vessel.

10. The method of claim 9 further comprising the step of withdrawing blood from the blood vessel.

11. The method of claim 10 further comprising the step of treating the blood to form a closure material capable of stopping blood flow.

12. The method of claim 11 further comprising the step of injecting the material into the vascular access.

13. The method of claim 11 further comprising the step of injecting the closure material into the tissue tract.

14. The method of claim 10 further comprising the step of injecting the material into the blood vessel.

15. The method of claim 9 further comprising the step of withdrawing the sheath simultaneously with the closure device.

16. The method of claim 9 further comprising the step of withdrawing the sheath prior to activating the closure device.

17. A method of closing an opening in a body comprising:

making an opening in a blood vessel;

performing an intravascular procedure;

inserting a closure device into the opening in the blood vessel; and injecting closure material into the closure device while the closure device is located within the blood vessel.

18. The method of claim 17 wherein the closure material is made by a method comprising:

removing blood from the blood vessel; and treating the blood.

19. The method of claim 18 wherein the treated blood is injected into the vascular access.

20. The method of claim 17 wherein the closure material is injected into the blood vessel.

21. The method of claim 17 wherein the closure material is injected into a space outside the blood vessel opening.

22. The method of claim 17 comprising injecting the closure material while the closure device is removed from the opening in the body.

\* \* \* \* \*

UNITED STATES PATENT AND TRADEMARK OFFICE
CERTIFICATE OF CORRECTION

PATENT NO. : 6,569,185 B2
DATED : May 27, 2003
INVENTOR(S) : Ungs

It is certified that error appears in the above-identified patent and that said Letters Patent is hereby corrected as shown below:

<u>Title page,</u>
Insert Item [73], Assignee, should read -- Scimed Life Systems, Inc.
Maple Grove, MN (US) --

Signed and Sealed this

Twentieth Day of July, 2004

JON W. DUDAS
*Acting Director of the United States Patent and Trademark Office*